United States Patent [19]

Harrison et al.

[11] 4,206,305

[45] Jun. 3, 1980

[54] 7-(1,3-DITHIOLAN-2-IMINO)CEPHALOSPORANIC ACID DERIVATIVES

[75] Inventors: Boyd L. Harrison; Joseph E. Dolfini, both of Cincinnati, Ohio

[73] Assignee: Richardson-Merrell Inc., Wilton, Conn.

[21] Appl. No.: 19,417

[22] Filed: Mar. 12, 1979

[51] Int. Cl.$^2$ .......................................... C07D 501/18
[52] U.S. Cl. ...................................... 544/28; 424/246
[58] Field of Search .................................... 544/27, 28

[56] References Cited

U.S. PATENT DOCUMENTS

| | | | |
|---|---|---|---|
| 3,907,788 | 9/1975 | Nudelman | 260/243 C |
| 4,071,682 | 1/1978 | Dolfini et al. | 260/243 C |

Primary Examiner—Nicholas S. Rizzo
Attorney, Agent, or Firm—William J. Stein; Eugene O. Retter; George W. Rauchfuss, Jr.

[57] ABSTRACT

Novel 7-(1,3-dithiolan-2-imino)cephalosporin derivatives are described which are particularly useful for their antibacterial properties.

9 Claims, No Drawings

7-(1,3-DITHIOLAN-2-IMINO)CEPHALOSPORANIC ACID DERIVATIVES

DESCRIPTION

1. Technical Field

This invention relates to certain cephalosporin derivatives useful as antibacterial agents and to a method for their preparation.

2. Background Art

Compounds with a cephalosporin nucleus belong to a well-known family of antibiotics that have been widely used in recent years for the treatment of various infectious diseases. A number of commercially useful cephalosporin antibiotics have been obtained by varying the substitution at the 3-position of the cephalosporin nucleus and by various modifications of the side-chain substituents at the 7-position of the cephalosporin nucleus. The search continues, however, for new compounds which possess a broad spectrum of antibacterial activity and which possess a high degree of activity toward both gram-positive and gram-negative bacteria without causing undesirable contraindications when administered to humans.

In an effort to improve the properties of existing compounds, efforts have been directed towards the insertion of a 1,3-dithiolane ring directly onto the 7-position of the cephalosporin nucleus to produce compounds that are useful antibacterial agents. More particularly the preparation of cephalosporanic acid derivatives having a 1,3-dithiolan-2-imino moiety located at the 7-position of the cephalosporin nucleus provides novel cephalosporin derivatives that are effective against one or more gram-positive and gram-negative microorganisms. Accordingly, the compounds of the present invention are effective in the treatment of various infectious diseases caused by such gram-positive and gram-negative bacteria in poultry or in mammals, including man. The compounds disclosed herein are also suitable for use in certain topical germicidal preparations or as surface disinfectants.

SUMMARY OF THE INVENTION

In accordance with the present invention certain novel 7-(1,3-dithiolan-2-imino) derivatives of cephalosporanic acid are described, which are useful for their antibacterial properties. More particularly, the present invention relates to 7-(1,3-dithiolan-2-imino)cephalosporanic acid derivatives having the formula

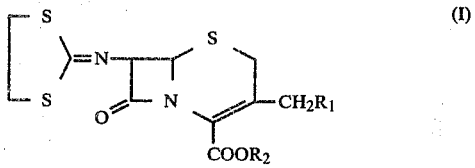

wherein $R_1$ is selected from the group consisting of hydrogen, hydroxy, acetoxy, 5-methyl-1,3,4-thiadiazol-2-ylthio, 1-methyl-1,2,3,4-tetrazol-5-ylthio and 1,2,3-triazol-4-ylthio; $R_2$ is selected from the group consisting of hydrogen, t-butyl, 2,2,2-trichloroethyl, benzhydryl, formyloxymethyl and alkanoyloxymethyl in which the alkanoyl group contains from 2 to 5 carbon atoms; and the pharmaceutically acceptable salts thereof.

Another aspect of the present invention relates to the preparation of these novel 7-(1,3-dithiolan-2-imino)- cephalosporanic acid derivatives by condensing in solution of an S-alkylated salt of 1,3-dithiolane-2-thione with a 7-aminocephalosporanic acid having the formula

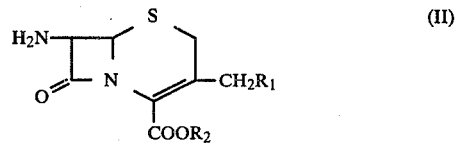

wherein the symbols $R_1$ and $R_2$ are as previously defined. This process is of particular advantage in that it provides, for the first time, a convenient method enabling the direct insertion of a 1,3-dithiolan-2-imino moiety at the 7-position of the cephalosporanic nucleus in good yield.

DETAILED DESCRIPTION OF THE INVENTION

As can be seen in formula (I) above, all of the derivatives of the present invention contain a 1,3-dithiolan-2-imino moiety attached to the 7-position of the cephalosporin nucleus. The term cephalosporanic acid derivatives as used herein relates generically to the specific cephalosporanic acids defined by the various substituents on the 3-methyl group of the cephalosporin nucleus. Thus, where the symbol $R_1$ is hydrogen, the compounds are designated as desacetoxycephalosporanic acids. When $R_1$ represents the hydroxyl group, the compounds are designated as belonging to the class of desacetylcephalosporanic acids. When the symbol $R_1$ represents the acetoxy group, the compounds are specifically designated as belonging to the class of cephalosporanic acids. Finally, the symbol $R_1$ can represent a heterocyclic thioether attached to the 3-methyl group of the cephalosporin nucleus. The preferred heterocyclic thioethers described herein include the 5-methyl-1,3,4-thiadiazol-2-ylthio group, the 1-methyl-1,2,3,4-tetrazol-5-ylthio group and the 1,2,3-triazol-4-ylthio group. In order to be consistent with the nomenclature employed, these heterocyclic thioethers are designated as 3-[(heterocycle-ylthio)methyl]decephalosporanic acids.

The compounds contemplated within the scope of this invention include not only the free cephalosporanic acids, but certain esters thereof as further indicated by the symbol $R_2$. Thus, where the symbol $R_2$ represents hydrogen, the free acid is designated. The preferred cephalosporanic acid ester groups include the t-butyl, 2,2,2-trichloroethyl, benzhydryl, formyloxymethyl and alkanoyloxymethyl groups. The term alkanoyl as used in this regard includes those groups having a total of from 2 to 5 carbon atoms, as for example, the acetyl, propionyl, butyryl, isobutyryl, 2-methylbutyryl, 3-methylbutyryl and 2,2-dimethylpropionyl groups. In general, these ester groups confer improved absorption properties upon the molecule, while remaining physiologically labile. Such esters are readily absorbed from the gastrointestinal tract, thereby promoting oral activity, whereupon they are enzymatically hydrolyzed to the corresponding free, and generally more active, cephalosporanic acids. Such esters are readily prepared in accordance with the procedures described by Binderup et al., Journal of Antibiotics, 24, 767 (1971).

The pharmaceutically acceptable salts of the compounds of formula (I) include the non-toxic, carboxylic acid salts that are formed with any suitable inorganic or organic base. Illustratively, these salts include those of alkali metals, as for example, sodium and potassium; alkaline earth metals, such as barium, calcium and magnesium; light metals of Group III A including aluminum; and organic primary, secondary and tertiary amines including triethylamine, procaine, dibenzylamine, vinylamine, N,N'-dibenzylethylenediamine, dihydroabietylamine, N-(lower)alkylpiperidine and various other amines that have been used to form non-toxic salts of antibiotics such as benzylpenicillin. These salts are prepared via conventional methods known to those skilled in the art, as for example by the neutralization of a solution of the free carboxylic acid in a polar solvent using a stoichiometric quantity of base, and recovering the salt therefrom.

Illustrative compounds encompassed by formula (I) above include:

7-(1,3-dithiolan-2-imino)cephalosporanic acid,
t-butyl 7-(1,3-dithiolan-2-imino)cephalosporanate,
2,2,2-trichloroethyl 7-(1,3-dithiolan-2-imino)cephalosporanate,
benzyhydryl 7-(1,3-dithiolan-2-imino)cephalosporanate,
formyloxymethyl 7-(1,3-dithiolan-2-imino)cephalosporanate,
pivaloyloxymethyl 7-(1,3-dithiolan-2-imino)cephalosporanate,
7-(1,3-dithiolan-2-imino)desacetylcephalosporanic acid,
t-butyl 7-(1,3-dithiolan-2-imino)desacetylcephalosporanate,
benzhydryl 7-(1,3-dithiolan-2-imino)desacetylcephalosporanate,
acetyloxymethyl 7-(1,3-dithiolan-2-imino)desacetylcephalosporanate,
butyryloxymethyl 7-(1,3-dithiolan-2-imino)desacetylcephalosporanate,
7-(1,3-dithiolan-2-imino)desacetoxycephalosporanic acid,
t-butyl 7-(1,3-dithiolan-2-imino)desacetoxycephalosporanate,
2,2,2-trichloroethyl 7-(1,3-dithiolan-2-imino)desacetoxycephalosporanate,
formyloxymethyl 7-(1,3-dithiolan-2-imino)desacetoxycephalosporanate,
pivaloyloxymethyl 7-(1,3-dithiolan-2-imino)desacetoxycephalosporanate,
7-(1,3-dithiolan-2-imino)-3-[(5-methyl-1,3,4-thiadiazol-2-ylthio)methyl]decephalosporanic acid,
t-butyl 7-(1,3-dithiolan-2-imino)-3-[(5-methyl-1,3,4-thiadiazol-2-ylthio)methyl]decephalosporanate,
benzhydryl 7-(1,3-dithiolan-2-imino)-3-[(5-methyl 1,3,4-thiadiazol-2-ylthio)methyl]decephalosporanate,
acetyloxymethyl 7-(1,3-dithiolan-2-imino)-3-[(5-methyl-1,3,4-thiadiazol-2-ylthio)methyl]decephalosporanate,
2-methylbutyryloxymethyl 7-(1,3-dithiolan-2-imino)-3-[(5-methyl-1,3,4-thiadiazol-2-ylthio)methyl]decephalosporanate,
7-(1,3-dithiolan-2-imino)-3-[(1-methyl-1,2,3,4-tetrazol-5-ylthio)methyl]decephalosporanic acid,
t-butyl 7-(1,3-dithiolan-2-imino)-3-[(1-methyl-1,2,3,4-tetrazol-5-ylthio)methyl]decephalosporanate.
2,2,2-trichloroethyl 7-(1,3-dithiolan-2-imino)-3-[(1-methyl-1,2,3,4-tetrazol-5-ylthio)methyl]decephalosporanate,
formyloxymethyl 7-(1,3-dithiolan-2-imino)-3-[(1-methyl-1,2,3,4-tetrazol-5-ylthio)methyl]decephalosporanate,
pivaloyloxymethyl 7-(1,3-dithiolan-2-imino)-3-[(1-methyl-1,2,3,4-tetrazol-5-ylthio)methyl]decephalosporanate,
7-(1,3-dithiolan-2-imino)-3-[(1,2,3-triazol-4-ylthio)methyl]decephalosporanic acid,
t-butyl 7-(1,3-dithiolan-2-imino)-3-[(1,2,3-triazol-4-ylthio)methyl]decephalosporanate,
benzhydryl 7-(1,3-dithiolan-2-imino)-3-[(1,2,3-triazol-4-ylthio)methyl]decephalosporanate,
acetyloxymethyl 7-(1,3-dithiolan-2-imino)-3-[(1,2,3-triazol-4-ylthio)methyl]decephalosporanate, and
3-methylbutyryloxymethyl 7-(1,3-dithiolan-2-imino)-3-[(1,2,3-triazol-4-ylthio)methyl]decephalosporanate.

The compounds represented by claim 1 are readily prepared in good yield by condensing an S-alkylated salt of 1,3-dithiolane-2-thione (III) with a 7-aminocephalosporanic acid. This reaction sequence is indicated as follows wherein the symbols $R_1$ and $R_2$ are as previously defined and the symbol X represents a halogen atom selected from the group consisting of chlorine, bromine and iodine.

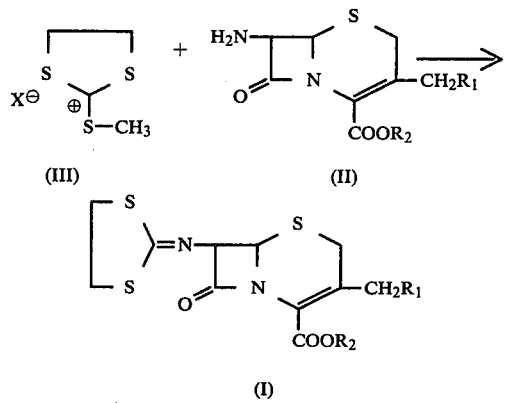

The S-alkylated salts of 1,3-dithiolane-2-thione are readily prepared by the alkylation of 1,3-dithiolane-2-thione, which is known commercially as ethylenetrithiocarbonate. Thus, for example, the addition of a methyl halide with stirring to a solution of 1,3-dithiolane-2-thione at a temperature ranging from 0° to about 20° C. for a period of from 1 to 24 hours results in the formation of the corresponding S-methyl halide salt of 1,3-dithiolane-2-thione as a crystalline salt. The S-methyl iodide salt of 1,3-dithiolane-2-thione is the alkylated salt of choice and is prepared by the addition of methyl iodide to a solution of 1,3-dithiolane-2-thione. Preferably, the reaction is conducted via the dropwise addition of methyl iodide to a nitromethane solution of 1,3-dithiolane-2-thione at room temperature under an inert atmosphere such as nitrogen or argon.

The various 7-aminocephalosporanic acids employed herein (II) are well-known compounds previously described in the literature. Thus, hydrolysis of cephalosporin C results in the formation of 7-aminocephalosporanic acid as described by Loder et al., Biochem. J. 79, 408–16 (1961) and represented by the formula

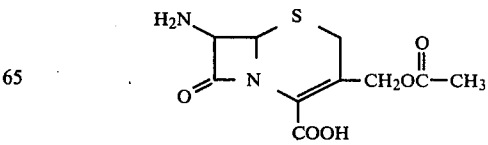

The compound 7-aminodesacetoxycephalosporanic acid, having the formula

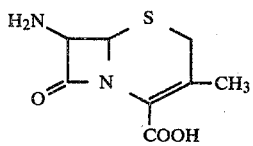

is prepared by the catalytic reduction of cephalosporin C, followed by the hydrolytic removal of the 5-aminoadipoyl side chain as described in U.S. Pat. No. 3,129,224.

Treatment of cephalosporin C with an acetyl esterase prepared from orange peel as described by Jeffery et al., Biochem J. 81, 591 (1961) results in the formation of 3-hydroxymethyl-7-aminodecephalosporanic acid, as designated herein, or 7-aminodesacetylcephalosporanic acid, which has the formula

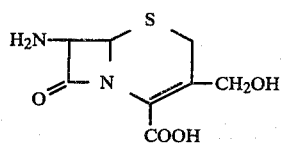

The 7-aminocephalosporanic acid derivatives (II) are readily condensed as their free acids to form the 7-(1,3-dithiolan-2-imino)cephalosporanic acid derivatives (I) of the present invention. Preferably, however, they are condensed in the form of their salts or their esters. Suitable salts include the sodium and trialkylamine salts, in which the alkyl group contains from 1 to 5 carbon atoms. Suitable esters include any of the esters disclosed in U.S. Pat. No. 3,284,451, or any of the silyl esters analogously disclosed in U.S. Pat. No. 3,249,622. The condensed esters are readily isolated to yield the products of the present invention or, as in the case of the silyl esters, they are readily cleaved to yield the free acids of the various 7-(1,3-dithiolan-2-imino)cephalosporanic acid derivatives.

In general, the condensation of the 7-aminocephalosporanic acid derivatives (II) and the S-alkylated salts of 1,3-dithiolan-2-thione (III) is conducted in the presence of a suitable solvent at temperatures ranging from $-30°$ C. to 100° C. The reaction time varies from 15 minutes to as long as 36 hours depending upon the particular reaction temperature employed. For convenience, the reaction is preferably conducted at room temperature or slightly below for a period of from 1 to 8 hours.

Suitable solvents in which the condensation takes place include acetone, acetonitrile, dioxane, dimethylformamide, chloroform, ethylene chloride, dichloromethane and tetrahydrofuran with acetonitrile being the particular solvent of choice. In certain instances, as when the 7-aminocephalosporanic acid starting materials are present in the form of a salt, mixtures of water and a miscible organic solvent may be advantageously employed. Optionally, the condensation can be conducted in the presence of an inert atmosphere, as for example argon or nitrogen gas. An excess of the S-alkylated salt of 1,3-dithiolane-2-thione (III) is also favorably employed to insure completeness of the reaction and to favor the yield of desired product obtained.

Following completion of the condensation reaction, the reaction mixture is generally quenched in water and the desired 7-(1,3-dithiolan-2-imino)cephalosporanic acid derivatives isolated via standard procedures known to those versed in the art. Thus, for example, the quenched reaction mixture is extracted with a suitable organic solvent, such as chloroform, methylene choride or ether, the organic extract is washed with a dilute aqueous acid solution to remove any unreacted starting material, the washed organic extract is dried, concentrated and the desired 7-(1,3-dithiolan-2-imino)cephalosporanic acid derivatives recovered therefrom. Purification of the products is generally effected by recrystallization from suitable organic solvents such as chloroform or from a chloroform-ether mixture.

Where the 7-aminocephalosporanic acid derivatives used as starting materials (II) are present as the free acid, i.e., where the symbol $R_2$ is hydrogen, the use of a silylating agent is advantageously employed. Under these circumstances the condensation best proceeds under anhydrous conditions in anhydrous solvents in which the free acids are not too soluble. The silylating agents employed form labile silyl esters with the various 7-aminocephalosporanic acids and are readily soluble in anhydrous solvents. Inasmuch as these silyl esters are highly sensitive to moisture, once condensation has taken place, the esters are readily hydrolyzed to the free acid by quenching the reaction mixture in water. Suitable silylating agents that may be favorably employed include various alkyl chlorosilanes, alkyl disilazanes, alkyl silylamines and alkylsilylamides, as for example triethyl chlorosilane, tri-n-butyl chlorosilazane, dimethylethyl chlorosilane, phenylethylmethyl chlorosilane, triphenyl chlorosilane, tetraethyldimethyl disilazane, hexamethyl disilazane, tetramethyldiphenyl disilazane, hexaphenyl disilazane, N-ethyl triethyl silylamine, triphenyl silylamine, N-trimethylsilylacetamide with the silylating agent of choice being O,N-bis-trimethylsilylacetamide.

In general, the free acids of the 7-aminocephalosporanic acid free derivatives (II), are suspended in a suitable anhydrous solvent, as for example acetonitrile, tetrahydrofuran or dioxane. Two equivalents of the silylating agent are added to this suspension and stirring is continued until esterification and solution occur, generally in about two hours or less at room temperature. An additional 10% excess of the silylating agent is added to insure complete esterification of the particular 7-aminocephalosporanic acid employed. Condensation with an S-alkylated salt of 1,3-dithiolane-2-thione and the subsequent isolation of the desired products remain essentially as previously described.

A preferred group of 7-(1,3-dithiolan-2-imino)cephalosporanic acid derivatives are those containing a methylthioheterocycle group at the 3-position of the cephalosporin nucleus. In addition to the condensation procedure described above, these compounds can be prepared by the displacement of the 3-acetoxy group of a salt or ester of 7-(1,3-dithiolan-2-imino)cephalosporanic acid. This displacement or solvolysis of the acetoxy group at the 3-methyl position of the cephalosporin nucleus is a well-known reaction described in U.S. Pat. Nos. 3,516,997 and 3,641,021. The acetoxy group is readily displaced with a heterocyclic thiol, such as 5-methyl-1,3,4-thiadiazol-2-ylthio, 1-methyl-1,2,3,4-tetrazol-5-thiol or 1,2,3-triazol-4-thiol at temperatures ranging from about 25° C. to 150° C. in aqueous solvents such as water or buffered aqueous solutions. Preferably, a temperature range of from 50° C. to 100° C. is employed in combination with a buffered aqueous solution having a pH ranging from 4.0 to 9.0. Suitable aqueous solutions include those selected from the group consisting of water, or an aqueous solution of acetone, tetrahydrofuran and dimethylformamide.

In certain instances the displacement of the acetoxy group from the methyl group at the 3-position results in the migration of the double bond to the 3-position of the β-lactam nucleus. Under those circumstances the position of the double bond can be re-established by the oxidation of the ring sulfur to the sulfoxide with such oxidizing agents as hydrogen peroxide, sodium metaperiodate or an organic peracid. Subsequent reduction of the sulfoxide by means of catalytic hydrogenation or sodium dithionite provides the desired cephalosporin derivatives which are unsaturated in the $\Delta^2$-position of the cephalosporin nucleus.

The novel compounds of the present invention are useful antimicrobial agents having a broad spectrum of anitmicrobial activity in vitro against standard laboratory microorganisms that are routinely used to demonstrate activity against pathogenic bacteria. The antibacterial spectrum of typical compounds described herein is determined in a standard manner by means of a qualitative diffusion assay as illustrated in Example 7 below. The in vitro antibacterial activity of the novel compounds of this invention not only makes them useful as pharmacological agents per se, but makes them useful as additives for animal feeds, as well as additives for materials which are subject to microbial deterioration, such as cutting oils and fuel oils. These compounds are also useful for their antibacterial effect in soaps, shampoos and in topical compositions for the treatment of wounds and burns.

The invention described herein is more particularly illustrated in conjunction with the following specific examples.

EXAMPLE 1

S-Methyl 1,3-dithiolane-2-thione iodide 1,3-Dithiolane-2-thione, (ethylenetrithiocarbonate) 13.6 g, is dissolved in 25 ml of reagent nitromethane and treated at room temperature with 14.2 g of methyl iodide via dropwise addition with stirring under an atmosphere of nitrogen. The reaction mixture is wrapped with foil for light protection and stirring is continued overnight. The crystals that form are filtered, washed with dry benzene and dried in vacuo to yield 20.9 g of brown colored, crystalline S-methyl 1,3-dithiolane-2-thione iodide having a m.pt. of 80°-3° C.

EXAMPLE 2 t-Butyl 7-(1,3-dithiolan-2-imino)desacetoxycephalosporanate t-Butyl 7-aminodesacetoxycephalosporanate, 2.7 g, is dissolved in 50 ml of dry acetonitrile, and 6.02 g of S-methyl 1,3-dithiolane-2-thione iodide, prepared in accordance with the preceding Example, is added with stirring thereto. Stirring is continued at room temperature for approximately 16 hours. The reaction mixture is filtered, quenched in water and the aqueous mixture extracted with chloroform. The chloroform extracts are combined, washed with a dilute 0.1 N solution of hydrochloric acid, dried over anhydrous MgSO$_4$, filtered and concentrated to dryness in vacuo. The residue is recrystallized from a hot chloroform solution to yield approximately 1.62 g of off-white colored t-butyl 7-(1,3-dithiolan-2-imino)desacetoxycephalosporanate having a m.pt. of 180°-181° C.

Following essentially the same procedure and substituting 2,2,2-trichloroethyl 7-aminocephalosporanate, formyloxymethyl 7-amino-3-[(5-methyl-1,3,4-thiadiazol-2-ylthio)methyl]decephalosporanate and pivaloyloxymethyl 7-amino-3-[(1-methyl-1,2,3,4-tetrazol-5-ylthio)methyl]decephalosporanate for the t-butyl 7-aminodesacetoxycephalosporanate above results in the formation of 2,2,2-trichloroethyl 7-(1,3-dithiolan-2-imino)cephalosporanate, formyloxymethyl 7-(1,3-dithiolan-2-imino)-3-[(5-methyl-1,3,4-thiadiazol-2-ylthio)methyl]decephalosporanate and pivaloyloxymethyl 7-(1,3-dithiolan-2-imino)-3-[(1-methyl-1,2,3,4-tetrazol-5-ylthio)methyl]decephalosporanate, respectively.

EXAMPLE 3

7-(1,3-Dithiolan-2-imino)desacetoxycephalosporanic acid

The compound 7-aminodesacetoxycephalosporanic acid, 4.55 g, is suspended with stirring in 120 ml of dry acetonitrile under a blanket of argon gas and 5.8 ml of bis-trimethylsilylacetamide added thereto. Stirring is continued for approximately 2 hours until solution occurs and 6.95 g of S-methyl 1,3-dithiolan-2-thione iodide is added together with an addition 30 ml of dry acetonitrile. The reaction mixture is stirred at room temperature for an additional hour quenched in 250 ml of water, and extracted with chloroform. The combined chloroform extracts are washed once with a saturated NaCl solution, dried over anhydrous MgSO$_4$, filtered and evaporated to dryness in vacuo. The residue is triturated with ether and is crystallized from an acetone-ether solution to yield 2.80 g of an off-white crystalline material having a m.pt. of 176°-7° C. (dec.), whose infrared and nuclear magnetic resonance spectra are consistent with that of the desired 7-(1,3-dithiolan-2-imino)desacetoxycephalosporanic acid.

Following essentially the same procedure, but substituting 7-aminodesacetylcephalosporanic acid, and 7-amino-3-[(1,2,3-triazol-4-ylthio)methyl]decephalosporanic acid for the 7-aminodesacetoxycephalosporanic acid above results in the formation of 7-(1,3-dithiolan-2-imino)desacetylcephalosporanic acid, and 7-(1,3-dithiolan-2-imino)-3-[(1,2,3-triazol-4-ylthio)methyl]decephalosporanic acid, respectively.

EXAMPLE 4

7-(1,3-Dithiolan-2-imino)cephalosporanic acid

The compound 7-aminocephalosporanic acid, 0.27 g, is suspended in 20 ml of dry acetonitrile, treated with 0.23 ml of bis-trimethylsilylacetamide under a blanket of argon gas and stirred for approximately 2 hours at room temperature until solution occurs. The compound S-methyl 1,3-dithiolane-2-thione iodide, 0.30 g, is added to the silyl ester solution and stirring is continued overnight at room temperature. The reaction mixture is quenched in water and the aqueous mixture is extracted with chloroform. The combined chloroform extracts are washed with a saturated solution of sodium chloride, dried over anhydrous MgSO$_4$, filtered and evaporated to dryness in vacuo to yield a yellowish-brown residue. Crystallization of this material from acetone-methanol-ether affords 0.193 g of 7-(1,3-dithiolan-2-imino)cephalosporanic acid having a m.pt. of 167°-9° C. (dec).

Following essentially the same procedure but substituting 7-amino-3-[(5-methyl-1,3,4-thiadiazol-2-ylthio)methyl]decephalosporanic acid and 7-amino-3-[(1-methyl-1,2,3,4-tetrazol-5-ylthio)methyl]decephalosporanic acid for the 7-aminocephalosporanic acid above, results in the formation of 7-(1,3-dithiolan-2-imino)-3-[(5-methyl-1,3,4-thiadiazol-2-ylthio)methyl]decephalosporanic acid and 7-(1,3-dithiolan-2-imino)-3-[(1-methyl-1,2,3,4-tetrazol-5-ylthio)methyl]decephalosporanic acid, respectively.

EXAMPLE 5

Benzhydryl 7-(1,3-dithiolan-2-imino)desacetoxycephalosporanate

The compound 7-(1,3-dithiolan-2-imino)desacetoxycephalosporanic acid prepared in accordance with the procedure of Example 3, 6.2 g, is dissolved in 250 ml of dry tetrahydrofuran, and treated with 4.0 g of diphenyldiazomethane. The purple reaction mixture is stirred at room temperature for a period of 24 hours, treated with activated charcoal, filtered and the filtrate evaporated to dryness in vacuo. Trituration of the residue so obtained using a 50% acetone/ether solution yields approximately 8.8 g of a yellow powder. Recrystallization of this material using a chloroform-ether solution yields the desired benzhydryl 7-(1,3-dithiolan-2-imino)desacetoxycephalosporanate as an off-white powder having a m.pt. of 160°–2° C.

Following essentially the same procedure but substituting 7-(1,3-dithiolan-2-imino)cephalosporanic acid for the 7-(1,3-dithiolan-2-imino)desacetoxycephalosporanic acid above results in the formation of benzhydryl 7-(1,3-dithiolan-2-imino)cephalosporanate as an off-white solid having a m.pt. of 200°–2° C.

EXAMPLE 6

7-(1,3-Dithiolan-2-imino)desacetoxycephalosporanic acid

Triethylamine, 5 ml, and 7-aminodesacetoxycephalosporanic acid, 2.14 g., are dissolved at room temperature in 20 ml of sieve-dried dimethylformamide under an atmosphere of argon gas. To this solution is added 3.06 g of S-methyl 1,3-dithiolane-2-thione iodide in portions. The reaction mixture is stirred at room temperature for a period of 2 hours and quenched into 150 ml of water. The quenched reaction mixture is extracted with four 50 ml portions of methylene dichloride followed by an additional extraction with a 100 ml portion of diethyl ether. The aqueous solution is adjusted to a pH of 2.5 using a 1 N solution of hydrochloric acid and extracted with three 100 ml portions of chloroform. The combined chloroform extracts are washed with a saturated NaCl solution, dired over anhydrous MgSO₄ and the dried organic extracts are evaporated to dryness in vacuo to yield a solid foam. Trituration of this foam with diethyl ether yields 7-(1,3-dithiolan-2-imino)desacetoxycephalosporanic acid as previously described in Example 3.

EXAMPLE 7

The following example illustrates the in vitro activity of the compounds of this invention.

Trypticase soy broth is inoculated from a slant culture of the test bacterium the day prior to testing. The inoculated broth is incubated for 24 hours at 37° C. and 0.05 ml of the inoculated and incubated broth is added to 25 ml of melted (45°–50° C.) trypticase soy agar. The seeded agar is poured into a 100 mm square petri dish and allowed to solidify.

Approximately 1 to 3 mg of purified 7-(1,3-dithiolan-2-imino)cephalosporanic acid is placed directly upon the agar and the agar plate incubated overnight. Chloramphenicol is similarly applied to seeded agar as a reference standard and incubated overnight. The agar plates are examined for clear zones of bacterial growth inhibition. The diameter of each zone is measured and recorded.

The following table summarizes the various zones of inhibition expressed in millimeters observed for the various test organisms.

| Organism | 7-(1,3-dithiolan-2-imino)cephalosporanic acid(mm) | chloramphenicol(mm) |
|---|---|---|
| *Staphylococcus aureus* | 4 | 29 |
| *Streptococcus faecalis* | 7 | 39 |
| *Salmonella schottmuelleri* | 4 | 39 |
| *Proteus mirabilis* | 3 | 35 |
| *Pseudomonas aeruginosa* | 7 | 26 |
| *Escherichia coli* | 30 | 52 |

Following essentially the same procedure the following zones of inhibition were observed for the test compound 7-(1,3-dithiolan-2-imino)desacetoxycephalosporanic acid.

| Organism | 7-(1,3-dithiolan-2-imino)desacetoxycephalosporanic acid(mm) | chloramphenicol(mm) |
|---|---|---|
| *Staphylococcus aureus* | 6 | 34 |
| *Streptococcus faecalis* | 4 | 25 |
| *Salmonella schottmuelleri* | 4 | 33 |
| *Proteus mirabilis* | 4 | 25 |
| *Pseudomonas aeruginosa* | 4 | 18 |
| *Escherichia coli* | 7 | 39 |
| *Streptococcus pyogenes* | 6 | 40 |

We claim:

1. A 7-(1,3-dithiolan-2-imino)cephalosporanic acid derivative having the formula

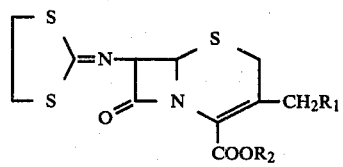

wherein
R₁ is selected from the group consisting of hydrogen, hydroxy and acetoxy;
R₂ is selected from the group consisting of hydrogen, t-butyl, 2,2,2-trichloroethyl, benzhydryl, formyloxymethyl and alkanoyloxymethyl in which the alkanoyl group contains from 2 to 5 carbon atoms; and
the pharmaceutically acceptable salts thereof.

2. A compound according to claim 1 wherein R₁ is hydrogen.

3. A compound according to claim 1 wherein R₁ is acetoxy.

4. A compound according to claim 1 which is 7-(1,3-dithiolan-2-imino)cephalosporanic acid.

5. A compound according to claim 1 which is diphenylmethyl 7-(1,3-dithiolan-2-imino)cephalosporanic acid.

6. A compound according to claim 1 which is 7-(1,3-dithiolan-2-imino)desacetoxycephalosporanic acid.

7. A compound according to claim 1 which is t-butyl 7-(1,3-dithiolan-2-imino)desacetoxycephalosporanate.

8. A process for the preparation of a 7-(1,3-dithiolan-2-imino)cephalosporanic acid derivative of claim 1 which comprises condensing in solution an S-alkylated salt of 1,3-dithiolane-2-thione with a 7-aminocephalosporanic acid having the formula

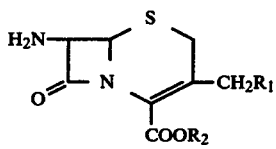

wherein the symbols $R_1$ and $R_2$ are defined as in claim 1, and recovering the cephalosporanic acid derivative therefrom.

9. A process for the preparation of a 7-(1,3-dithiolan-2-imino)cephalosporanic acid derivative of claim 1 in which $R_2$ is hydrogen, which comprises condensing in solution an S-alkylated salt of 1,3-dithiolane-2-thione with a silyl ester of a 7-aminocephalosporanic acid having the formula

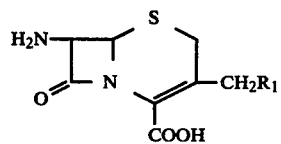

wherein the symbol $R_1$ is as defined in claim 1, and recovering the cephalosporanic acid derivative therefrom.

* * * * *